(12) United States Patent  
Zagorchev et al.

(10) Patent No.: US 11,202,677 B2  
(45) Date of Patent: Dec. 21, 2021

(54) TREATMENT TRAJECTORY GUIDANCE SYSTEM

(71) Applicant: KONINKLIJKE PHILIPS N.V., Eindhoven (NL)

(72) Inventors: Lyubomir Georgiev Zagorchev, Burlington, MA (US); Joel Haaf, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 476 days.

(21) Appl. No.: 16/152,550

(22) Filed: Oct. 5, 2018

(65) Prior Publication Data

US 2019/0105105 A1   Apr. 11, 2019

Related U.S. Application Data

(60) Provisional application No. 62/569,369, filed on Oct. 6, 2017.

(51) Int. Cl.
*G16H 20/40* (2018.01)
*G16H 40/60* (2018.01)
(Continued)

(52) U.S. Cl.
CPC ............ *A61B 34/10* (2016.02); *A61B 5/0042* (2013.01); *A61B 5/055* (2013.01); *A61B 5/4064* (2013.01);
(Continued)

(58) Field of Classification Search
CPC ... A61B 34/20; A61B 34/10; A61B 2034/102; A61B 2034/104–105;
(Continued)

(56) References Cited

U.S. PATENT DOCUMENTS 9,220,458 B2   12/2015   Pouratian
9,256,951 B2   2/2016   Zagorchev
(Continued)

FOREIGN PATENT DOCUMENTS

WO   WO-2014139022 A1 *   9/2014   ......... A61B 5/14539
WO   WO2016058075 A1   4/2016
(Continued)

OTHER PUBLICATIONS

Essert et al., "Automatic computation of electrode trajectories for Deep Brain Stimulation: a hybrid symbolic and numerical approach" Int J CARS (2012) 7:517-532 (Year: 2012).*

(Continued)

*Primary Examiner* — Boniface N Nganga
(74) *Attorney, Agent, or Firm* — Micah-Shalom Kesselman (57) ABSTRACT

Treatment trajectory guidance systems and methods are provided. In one embodiment, the method for treatment trajectory guidance in a patient's brain includes obtaining a three-dimensional (3D) brain model that includes a model of an anatomy, the model of the anatomy including a plurality of feature points; modifying the 3D brain model based on magnetic resonance (MR) data of the patient's brain from a magnetic resonance imaging (MRI) device to obtain a plurality of modified feature points on a modified model of the patient's anatomy in the patient's brain; displaying on a display a first planned trajectory for treating the patient's anatomy based on the plurality of modified feature points; and displaying, on the display, a first estimated treatment result for the first planned trajectory.

20 Claims, 7 Drawing Sheets
(4 of 7 Drawing Sheet(s) Filed in Color)

(51) Int. Cl.
| | |
|---|---|
| *G16H 50/00* | (2018.01) |
| *A61B 34/10* | (2016.01) |
| *A61B 5/055* | (2006.01) |
| *A61B 5/00* | (2006.01) |
| *G01R 33/50* | (2006.01) |
| *G06K 9/62* | (2006.01) |
| *G01R 33/56* | (2006.01) |
| *G09B 23/30* | (2006.01) |
| *G06K 9/00* | (2006.01) |
| *G16H 50/20* | (2018.01) |
| *A61B 34/20* | (2016.01) |
| *G06T 17/00* | (2006.01) |
| *A61B 18/00* | (2006.01) |
| *G06T 19/00* | (2011.01) |
| *G06T 19/20* | (2011.01) |
| *A61B 90/00* | (2016.01) |
| *A61B 6/00* | (2006.01) |

(52) U.S. Cl.
CPC ......... *G01R 33/50* (2013.01); *G01R 33/5608* (2013.01); *G06K 9/00214* (2013.01); *G06K 9/6206* (2013.01); *G09B 23/30* (2013.01); *G16H 20/40* (2018.01); *G16H 40/60* (2018.01); *G16H 50/20* (2018.01); *A61B 6/501* (2013.01); *A61B 2018/00446* (2013.01); *A61B 2018/00577* (2013.01); *A61B 2034/102* (2016.02); *A61B 2034/104* (2016.02); *A61B 2034/105* (2016.02); *A61B 2034/107* (2016.02); *A61B 2034/2051* (2016.02); *A61B 2090/374* (2016.02); *A61B 2576/026* (2013.01); *G01R 33/5602* (2013.01); *G06K 2209/051* (2013.01); *G06T 17/00* (2013.01); *G06T 19/00* (2013.01); *G06T 19/20* (2013.01); *G16H 50/00* (2018.01)

(58) Field of Classification Search
CPC ......... A61B 2034/107–108; A61B 2034/2051; A61B 2034/2064; A61B 5/501; A61B 5/4064; A61B 5/055; A61B 5/0042; A61B 6/501; A61B 2090/374; A61B 2576/026; A61B 2018/00577; A61B 2018/00446; G06K 9/00214; G06K 9/6206; G06K 2209/051; G06T 17/00; G06T 17/20; G09B 23/30; G16H 20/40; G16H 30/40; G16H 40/60; G16H 50/00; G16H 50/20
See application file for complete search history.

(56) References Cited

U.S. PATENT DOCUMENTS

| | | | |
|---|---|---|---|
| 9,568,580 | B2 | 2/2017 | Dale |
| 9,600,138 | B2 | 3/2017 | Thomas |
| 2008/0081982 | A1 | 4/2008 | Simon |
| 2008/0123922 | A1* | 5/2008 | Gielen ................ A61B 6/5241 382/131 |
| 2011/0040351 | A1* | 2/2011 | Butson ................ G16H 20/40 607/59 |
| 2012/0027278 | A1 | 2/2012 | Chaney |
| 2012/0184844 | A1* | 7/2012 | Gielen ................ A61B 6/5235 600/424 |
| 2013/0226261 | A1* | 8/2013 | Sparks ................ A61B 34/10 607/45 |
| 2014/0003696 | A1 | 1/2014 | Taghva |
| 2015/0146951 | A1 | 5/2015 | Zagorchev |
| 2016/0070436 | A1* | 3/2016 | Thomas ................ A61B 6/032 715/771 |
| 2016/0256069 | A1 | 9/2016 | Jenkins |
| 2017/0035320 | A1 | 2/2017 | Verma |
| 2017/0076452 | A1 | 3/2017 | Yui |

FOREIGN PATENT DOCUMENTS

| | | |
|---|---|---|
| WO | 2016119040 A1 | 8/2016 |
| WO | WO2017081302 A1 | 5/2017 |

OTHER PUBLICATIONS

Zagorchev, L. et al.,"Evaluation of Traumatic Brain Injury Patients Using a Shape-Constrained Deformable Model," in Multimodal Brain Image Analysis MBIA 2011, Lecture Notes in Computer Science, vol. 7012. Springer, Berlin, Heidelberg.

* cited by examiner

TREATMENT TRAJECTORY GUIDANCE SYSTEM

CROSS-REFERENCE TO RELATED APPLICATIONS

This patent application claims the priority benefit under 35 U.S.C. § 119(e) of U.S. Provisional Application No. 62/569,369 filed on Oct. 6, 2017, the contents of which are herein incorporated by reference.

TECHNICAL FIELD

The present disclosure relates generally to treatment trajectory guidance, and in particular, to devices, systems, and methods for planning trajectory of a treatment catheter using brain segmentations modified based on a high-resolution magnetic resonance scan and using the planned trajectory to guide the treatment.

BACKGROUND

Minimally invasive intervention has been increasingly used to treat brain tumors and medically intractable epilepsy. One of emergent minimally invasive intervention techniques is interstitial thermal therapy (LITT). In a LITT procedure, an ablation catheter delivers heat to target cells by emitting collimated light through a diffusing tip, heating the target cells to 40° C. or higher. When heated to a temperature between 40° C. and 60° C., the target cells suffer irreversible cell damage due to denaturation of their DNA. Target cells heated to above 60° C. die instantly. When the target cells are heated to above 100° C., water in the target cells vaporizes and surrounding tissues carbonize.

The most common form of medically intractable epilepsy is mesial temporal lobe epilepsy (MTLE). Of the minimally invasive LITT procedures, stereotactic laser-guided amygdalohippocampectomy (SLAH) is used to treat MTLE. During a SLAH procedure, a craniotomy is performed to create a hole in a patient's skull. A polycarbonate anchor bolt is fixed to the hole, through which an alignment rod is driven into the patient's brain to create a path to the ablation target at or near the amygdalohippocampal complex (AHC) of the patient. Once the path is created, the alignment rod is removed and a polycarbonate cooling catheter and a diode laser fiber is inserted along the path to the ablation target. Ablations are performed along the long axis of the AHC with real time visualization. Magnetic resonance thermometry is used to confirm the ablation result. As the AHC is located deep in the brain, the planning of the trajectory of the catheter is critical. Conventionally, trajectory planning is manual and a standardized protocol has to be followed. For those reasons, trajectory planning can be time-consuming and user-dependent. Compounding with variability of ablation volumes in different patients, achieving reproducible ablation path and volume to ensure postoperative seizure freedom can be difficult. Similarly, when a brain tumor or lesion is located deep in a patient's brain, planning an ablation trajectory to achieve reproducible ablation path and volume can be challenging.

SUMMARY

Embodiments of the present disclosure are configured to plan a treatment trajectory in a patient's brain by use of brain segmentations adapted to magnetic resonance (MR) data of a patient's brain. One of the brain segmentation techniques involves use of a three-dimensional (3D) brain model. The 3D brain model includes a model of an anatomy and the model of the anatomy includes feature points defining a specific trajectory. When the 3D brain model is modified based on the MR data of the patient's brain, the features points of the model are mapped to target locations in the patient's brain anatomy. The embodiments of the present disclosure display a planned trajectory for treating the patient's anatomy at the target locations and also display estimated treatment result for the planned trajectory. Treatment trajectory planning based on the modified feature points saves time and allows for reproducible treatment results. Aspects of the present disclosure advantageously provide a rapid and accurate treatment trajectory planning method and system.

In one embodiment, a method for treatment trajectory guidance in a patient's brain is provided. The method includes obtaining a three-dimensional (3D) brain model that includes a model of an anatomy, the model of the anatomy including a plurality of feature points; modifying, by use of a computing device in communication with an magnetic resonance imaging (MRI) device, the 3D brain model based on magnetic resonance (MR) data of the patient's brain from the MRI device to obtain a plurality of modified feature points on a modified model of the patient's anatomy in the patient's brain; displaying, on a display in communication with the computing device, a first planned trajectory for treating the patient's anatomy based on the plurality of modified feature points; and displaying, on the display, a first estimated treatment result for the first planned trajectory. In some embodiments, the first planned trajectory includes a first entry point into the patient's brain. In some implementations, the method further includes, in response to a first user input, displaying on the display a second planned trajectory different from the first planned trajectory; and displaying on the display a second estimated treatment result for the second planned trajectory.

In some embodiments, the method for treatment trajectory guidance in a patient's brain further includes obtaining, by use of the MRI device, an actual treatment trajectory during a treatment of the patient's anatomy; and displaying, on the display, the actual treatment trajectory along with the first planned trajectory. In some embodiments, the MR data include T1 weighted magnetic resonance (T1W MR) data of the patient's brain. In some implementations, the 3D brain model is a shape-constrained deformable brain model. In some instances, the plurality of feature points extend along a geometric midline of the model of the anatomy. In some instances, the patient's anatomy can include an amygdalo-hippocampal complex, an amygdala, a hippocampus, a lesion, or a tumor in the patient's brain.

In another embodiment, a treatment trajectory guidance system is provided. The treatment trajectory guidance system includes a computing device in communication with a magnetic resonance imaging (MRI) device. The computing device is operable to obtain a three-dimensional (3D) brain model that includes a model of an anatomy, the model of the anatomy including a plurality of feature points; receive magnetic resonance (MR) data of a patient's brain from the MRI device; modify the 3D brain model based on the MR data of the patient's brain to obtain a plurality of modified feature points on a modified model of the patient's anatomy; output, to a display in communication with the computing device, a first planned trajectory for treating the patient's anatomy based on the plurality of modified feature points; and output to the display a first estimated treatment result for the first planned trajectory. In some embodiments, the first planned trajectory includes a first entry point into the patient's brain. In some embodiments, the computing device is further operable to, in response to a first user input, display on the display a second planned trajectory different from the first planned trajectory; and display on the display a second estimated treatment result for the second planned trajectory.

In some embodiments, the computing device of the treatment trajectory guidance system is further operable to obtain, by use of the MRI device, an actual treatment trajectory during a treatment of the patient's anatomy; and output, to the display, the actual treatment trajectory along with the first planned trajectory. In some implementations, the treatment trajectory guidance system further includes the display and the MRI device. In some instances, the MR data include T1 weighted magnetic resonance (T1W MR) data of the patient's brain. In some embodiments, the brain model is a shape-constrained deformable brain model. In some implementations, the plurality of feature points extend along a geometric midline of the model of the anatomy. In some embodiments, the patient's anatomy can include an amygdalohippocampal complex, an amygdala, a hippocampus, a lesion, or a tumor in the patient's brain.

Other devices, systems, and methods specifically configured to interface with such devices and/or implement such methods are also provided.

Additional aspects, features, and advantages of the present disclosure will become apparent from the following detailed description along with the drawings.

BRIEF DESCRIPTIONS OF THE DRAWINGS

The patent or application file contains at least one drawing executed in color. Copies of this patent or patent application publication with color drawing(s) will be provided by the United States Patent & Trademark Office upon request and payment of the necessary fee. Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates.

Figure 1:
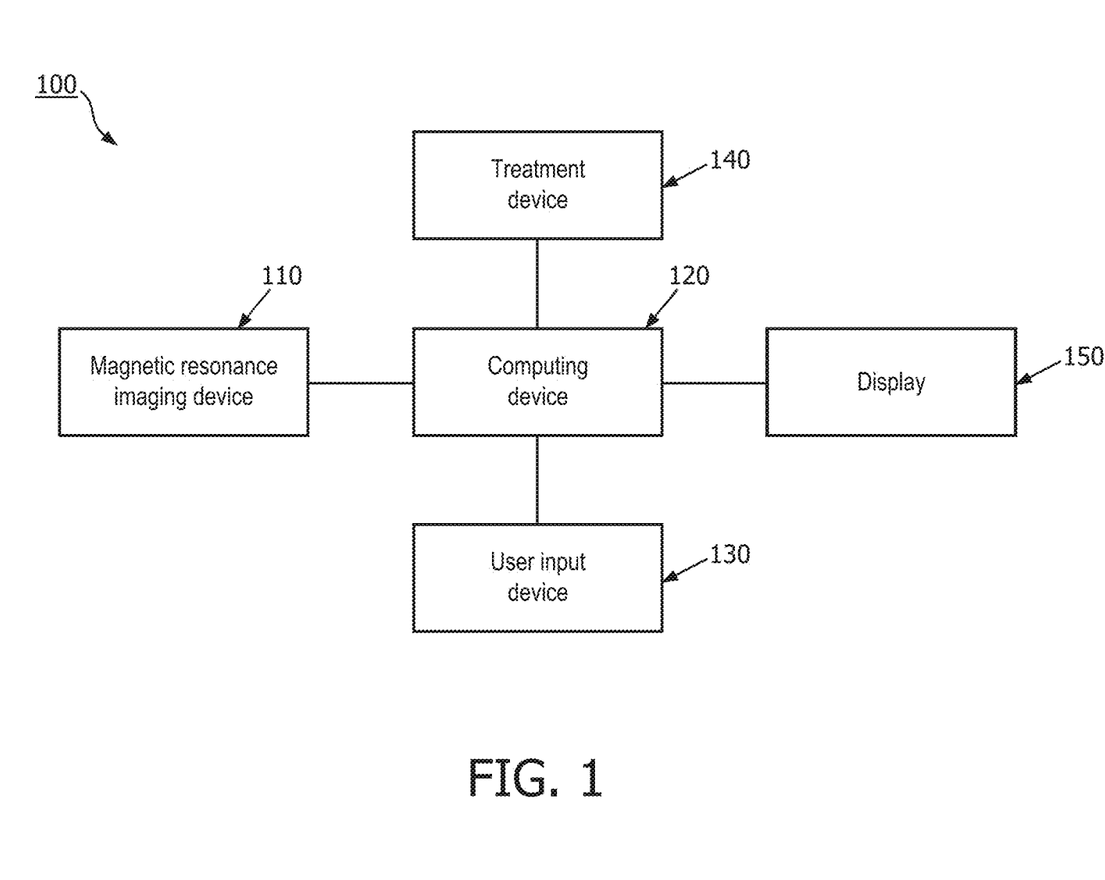
FIG. 1 is a schematic diagram of a system for treatment trajectory planning in a patient's brain, according to aspects of the present disclosure.

Referring now to FIG. 1, shown therein is a schematic diagram of a system 100 for ablation trajectory planning in a patient's brain, according to aspects of the present disclosure. The system 100 includes a computing device 120 connected to a magnetic resonance imaging (MRI) device 110, a user input device 130, a treatment device 140, and a display 150. The computing device 120 includes a processing circuit, such as one or more processors in communication with memory. The memory can be tangible computer readable storage media that stores instructions that are executable by the one or more processors. The computing device 120 can be a workstation or a controller that serves as an interface between the MRI device 110 and the treatment device 140. In some embodiments, the computing device 120 can receive magnetic resonance (MR) data, process the same and output MR image data to the display 150 such that the display 150 can display MR images. In some instances, the treatment device 140 includes a treatment catheter (ablation catheter) and a catheter driver. The treatment catheter can be an MRI-compatible ablation catheter used in an ablation treatment, an electrical stimulation catheter for an electrical stimulation treatment, a magnetic stimulation catheter for a magnetic stimulation treatment, a drug infusion catheter for a drug infusion treatment, and/or other suitable treatment device. The catheter driver can drive the treatment catheter into a patient's skull through a hole created in a craniotomy procedure. The user input device 130 serves as an interface between a user and the computing device 120 and allows the user interact with the computing device 120 by entering user inputs. The user input device 130 can be a keyboard, a mouse, a touchpad, a trackpad, a touchscreen mounted on the display 150, a hand gesture control device, or a virtual reality glove.

The system 100 can be used to plan and perform minimally invasive treatment procedures. For example, the system 100 can be used to plan and perform an ablation treatment using an MRI-compatible ablation catheter, an electrical stimulation treatment using an electrical stimulation catheter, a magnetic stimulation treatment using a magnetic stimulation catheter, or a drug infusion treatment using a drug infusion catheter. It is noted that while the embodiments of the present disclosure are described in conjunction with an MRI-compatible ablation catheter and an ablation treatment, the systems and methods can apply to plan and guide a treatment trajectory of a treatment catheter to a treatment target in a treatment other than an ablation treatment. In some embodiments, the system 100 can be used to plan and perform MRI-guided LITT procedures. The system 100 can help surgeons visualize and plan a trajectory of an ablation catheter of the treatment device 140 into a patient's skull, through the patient's brain, and on to an ablation target in the patient's brain. The computing device 120 can automatically segment the ablation target based on a segmentation protocol. In some embodiments, the computing device 120 can automatically segment the ablation target based on a three-dimensional (3D) brain. In those embodiments, the computing device 120 of the system 100 receives a 3D brain model from a storage media or through wired or wireless connection to a server or a remote workstation. In some instances, the 3D brain model can be stored in a storage device in the computing device 120 or a storage device retrievable by the computing device 120. In some implementations, the 3D brain model is a shape-constrained deformable brain model. In some instances, the 3D brain model may be the brain model described in "Evaluation of traumatic brain injury patients using a shape-constrained deformable model," by L. Zagorchev, C. Meyer, T. Stehle, R. Kneser, S. Young and J. Weese, 2011, in *Multimodal Brain image Analysis* by Liu T., Shen D., Ibanez L., Tao X. (eds). MBIA 2011. *Lecture Notes in Computer Science*, vol 7012. Springer, Berlin, Heidelberg, the entirety of which is hereby incorporated by reference. In some instances, the 3D brain model may be the deformable brain model described in U.S. Pat. No. 9,256,951, titled "SYSTEM FOR RAPID AND ACCURATE QUANTITATIVE ASSESSMENT OF TRAUMATIC BRAIN INJURY" or the shape-constrained deformable brain model described in U.S. Pat. App. Pub. No. 20150146951, titled "METHOD AND SYSTEM FOR QUANTITATIVE EVALUATION OF IMAGE SEGMENTATION," each of which is hereby incorporated by reference in its entirety.

The 3D brain model includes models of anatomies of a general human brain, including but not limited to models of an amygdalohippocampal complex (AHC), an amygdala, a hippocampus, a tumor, or a lesion. In some embodiments, each of the models of anatomies in the 3D brain model includes an indication of an optimal ablation trajectory. The indication can contain information such as volumes, angles, cross-sectional planes, geometric medial (midline) axis of the anatomy model. The indication of the optimal ablation trajectory can be modified based on to MR data of a patient's brain. For example, the ablation trajectory can be adapted to MR data of a patient's brain. In some embodiments, the indication includes a plurality of feature points. In some embodiments, the feature points are points of therapeutic importance or points where neurons are concentrated. In some instances, the feature points are points along a geometric midline of an anatomy. To adapt the 3D brain model to the volume and geometry of the patient's brain, MR data of the patient's brain is obtained by use of the MRI device 110 and the computing device 120 modifies the 3D brain model based on MR data of the patient's brain, resulting in a modified 3D brain model. As the 3D brain model includes models of anatomies of a general human brain, the modified 3D brain model also includes modified models of the patient's anatomies, including modified models of the patient's AHC, the patient's amygdala, the patient's hippocampus, the patient's tumor, and the patient's lesion. The computing device 120 can output the MR data, the modified 3D brain model, and the modified models of the patient's anatomies with modified feature points to the display 150, allowing the surgeon to visualize the patient's brain and anatomies therein. In some embodiments, the surgeon can use the user input device 130 to enter user inputs to manipulate the modified 3D brain model and the modified models of the patient's anatomies.

To plan a trajectory to ablate an anatomy of the patient's brain, the modified model of the patient's brain with modified feature points is displayed on the display 150, alone or together with other modified models of other anatomies of the patient's brain. In some embodiments, depending on design and geometric shape of the ablation catheter of the treatment device 140, the computing device 120 can calculate a preliminary planned trajectory of the ablation catheter to address the feature points and cause the preliminary planned trajectory to be displayed on the display 150 along with the modified model of the patient's anatomy. In some embodiments, the surgeon can enter user inputs using the user input device 130 to change the positions and angles of the preliminary planned trajectory to arrive at a planned trajectory. In some implementations, the computing device 120 can estimate an ablation result of the planned trajectory. To estimate the ablation result, the computing device 120 can take into account the energy input to the ablation catheter and the ablation time. In some instances, the planned trajectory includes an entry point into the patient's skull. The entry point is the point where the planned trajectory intersects with the patient's skull.

After the planned trajectory is determined, the surgeon inserts the ablation catheter of the treatment device 140 through the patient's skull and into the patient's brain. During the insertion of the ablation catheter, the MRI device 110 scans the patient's brain in real time and continuously sends the MR data to the computing device 120. The computing device 120 processes the MR data and outputs MR image data to the display 150 for display. This way, the surgeon can learn the progress of the insertion of the ablation catheter along the planned trajectory. In some embodiments, the computing device 120 can output the real-time MR image data containing the actual ablation trajectory and the planned trajectory to the display 150 such that the surgeon can compare the actual ablation trajectory and the planned trajectory.

Figure 2:
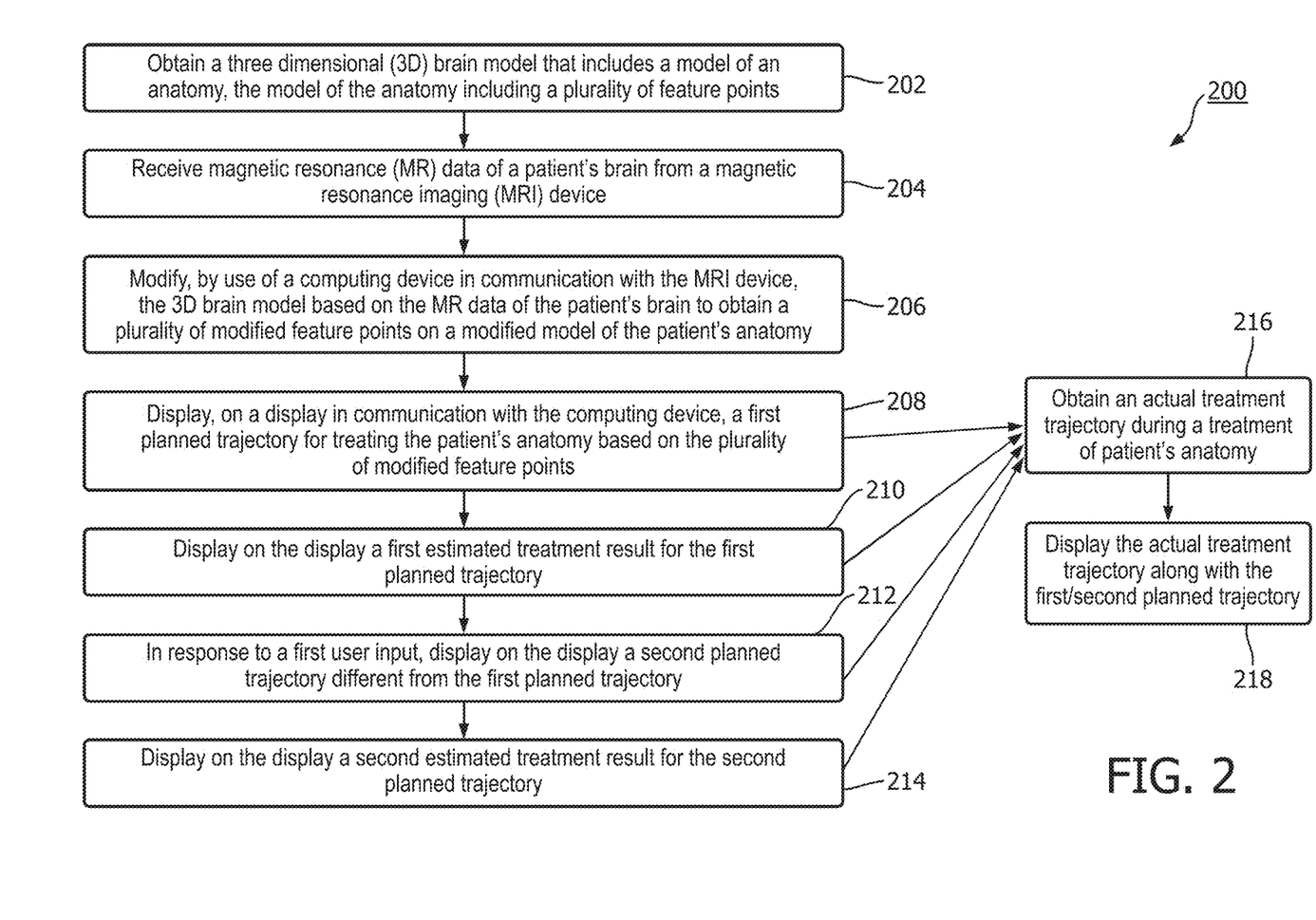
FIG. 2 is a flowchart illustrating a method of planning a treatment trajectory in a patient's brain, according to aspects of the present disclosure.

Referring now to FIG. 2, shown therein is a flowchart illustrating a method 200 of planning an ablation trajectory in a patient's brain, according to aspects of the present disclosure. The method 200 includes operations 202, 204, 206, 208, 210, 212, 214, 216, and 218. It is understood that the operations of method 200 may be performed in a different order than shown in FIG. 2, additional operations can be provided before, during, and after the operations, and/or some of the operations described can be replaced or eliminated in other embodiments. The operations of the method 200 can be carried out by a computing device in a treatment trajectory planning system, such as the computing device 120 of the system 100. The method will be described below with reference to FIGS. 3, 4, 5A, 5B, 5C, 6 and 7.

At operation 202 of the method 200, a 3D brain model is obtained. In some embodiments, the 3D brain model is a shape-constrained deformable brain model. In some instances, the 3D brain model may be the brain modes described in "Evaluation of traumatic brain injury patients using a shape-constrained deformable model," by L. Zagorchev, C. Meyer, T. Stehle, R. Kneser, S. Young and J. Weese, 2011, in. *Multimodal Brain image Analysis* by Liu T., Shen D., Ibanez L., Tao X. (eds). MBIA 2011. *Lecture Notes in Computer Science,* vol 7012. Springer, Berlin, Heidelberg, the entirety of which is hereby incorporated by reference. In some instances, the 3D brain model may be the deformable brain model described in U.S. Pat. No. 9,256, 951, titled "SYSTEM FOR RAPID AND ACCURATE QUANTITATIVE ASSESSMENT OF TRAUMATIC BRAIN INJURY" or the shape-constrained deformable brain model described in U.S. Pat. App. Pub. No. 20150146951, titled "METHOD AND SYSTEM FOR QUANTITATIVE EVALUATION OF IMAGE SEGMENTATION," each of which is hereby incorporated by reference in its entirety. In some implementations, the 3D brain model is stored in the computing device 120 or a storage device or medium retrievable by the computing device 120.

Figure 3:
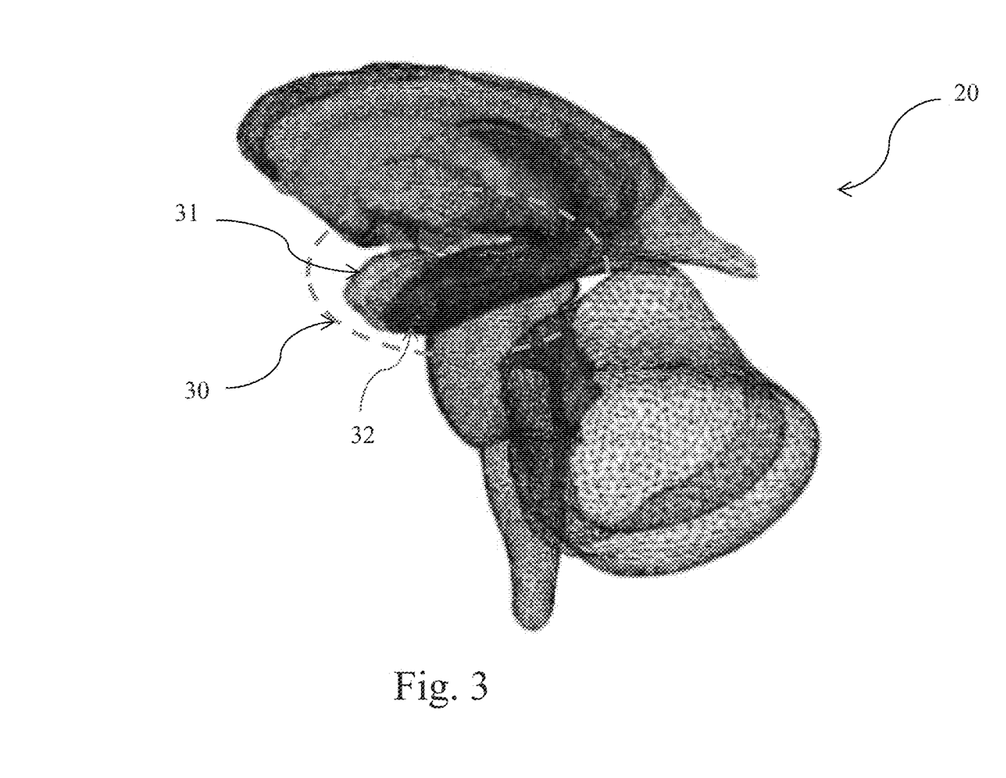
FIG. 3 is a schematic diagram of a 3D brain model of a human brain, according to aspects of the present disclosure.

In some embodiments, the 3D brain model is formed of a surface mesh that includes a plurality of triangularly shaped polygons, each of which includes three vertices and edges. In some other embodiments, the 3D brain model may be formed of polygons of other shapes. Referring now to FIG. 3, shown therein is a schematic diagram of a 3D brain model 20 of a human brain, according to aspects of the present disclosure. The 3D brain model 20 includes models of anatomies of a human brain, including a model of an AHC 30. The model of the AHC 30 includes a model of an amygdala 31 and a model of a hippocampus 32. Each of the models of the anatomies may include a plurality of feature points. In some embodiments, the feature points can be points of therapeutic importance or points where neurons are concentrated. For example, the model of the AHC 30 may include a plurality of feature points that fall on the geometric midline of the model of the AHC 30.

Figure 4:
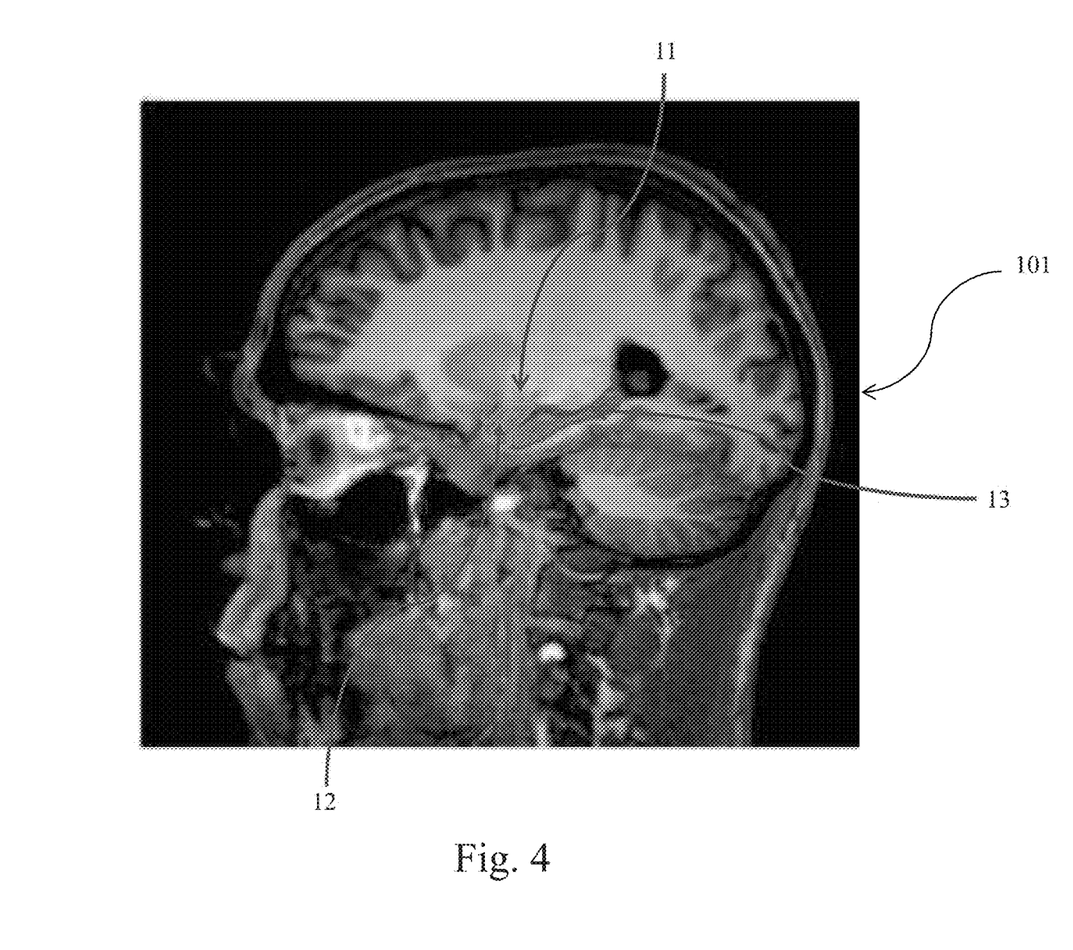
FIG. 4 is an MR image of a patient's brain showing the amygdalohippocampal complex (AHC), according to aspects of the present disclosure.

At operation 204 of the method 200, MR data of the patient's brain is received from the MRI device 110. The MR data of the patient's brain can be processed by the computing device 120, resulting in MR image data displayable by the display 150. FIG. 4 shows an MR image 101 of a patient's brain showing the patient's anatomies, including the AHC 11 of the patient. The patient's AHC 11 includes the patient's amygdala 12 and hippocampus 13. In some embodiments, the MR data includes T1 weighted magnetic resonance (T1W MR) data of the patient's brain. In some instances where the MR data is obtained before the ablation operation, the MR data can be referred to pre-operative MR data.

At operation 206 of the method 200, the computing device 120 modifies the 3D brain model based on the MR data of the patient's brain to obtain a plurality of modified feature points on a modified model of the patient's anatomy. In some embodiments, techniques utilized to modify the 3D brain model based on the MR data of the patient's brain include those disclosed in U.S. Pat. No. 9,256,951, titled "SYSTEM FOR RAPID AND ACCURATE QUANTITATIVE ASSESSMENT OF TRAUMATIC BRAIN INJURY," which is incorporated by reference in its entirety. In embodiments of the present disclosure, the modification of the 3D brain model based on the MR data of the patient's brain substantially ensures a one-to-one correspondence between the surface meshes of the modified 3D brain model to the same region of the patient's brain. In some instances, modifying the 3D brain model based on the MR data of the patient's brain includes adapting the 3D brain model to the MR data of the patient's brain.

Figure 5A:
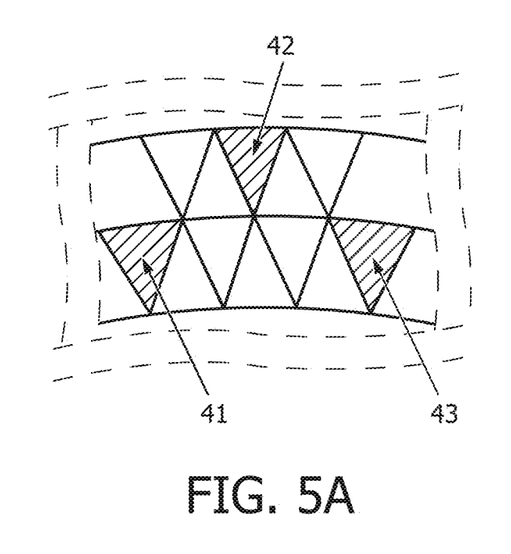
FIG. 5A is a schematic diagram of a part of a model of an anatomy with feature points, according to aspects of the present disclosure.
Figure 5B:
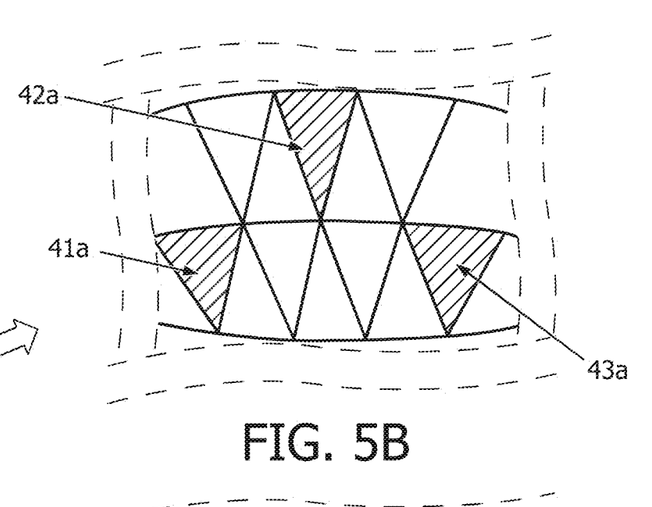
FIG. 5B is a schematic diagram of a part of a modified model of a first patient's anatomy with modified feature points, according to aspects of the present disclosure.
Figure 5C:
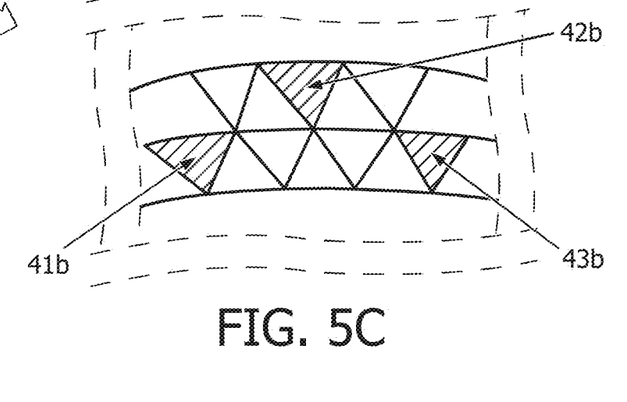
FIG. 5C is a schematic diagram of a part of a modified model of a second patient's anatomy with modified feature points, according to aspects of the present disclosure.

FIGS. 5A, 5B and 5C are schematic diagrams demonstrating what happens when a model of a human brain anatomy is modified based on the patient's anatomy in the MR data. FIG. 5A shows a part of a human brain anatomy with three feature points 41, 42 and 43. The human brain anatomy can be, for example, an AHC, an amygdala, a hippocampus, a tumor, or a lesion. FIG. 5B is a schematic diagram of the human brain anatomy model modified based on the MR data of a first patient's anatomy. That is, FIG. 5E is a modified model of the first patient's anatomy. As is shown in FIG. 5B, the triangular polygons deform and expand to adapt to or match to the MR data of the first patient's anatomy. While the triangular polygons deformed and expanded, the feature points 41, 42 and 43 become the modified feature points 41a, 42a and 43a. Although modified feature points 41a, 42a and 43a are of different geometric shapes in FIG. 5B, they generally maintain their relative positions. When the model of the anatomy in FIG. 5A is modified based on the MR data of the anatomy of a different patient—a second patient, the triangular polygons deform and contract, as shown in FIG. 5C. Although the modified feature points 41b, 42h and 43b are of geometric shapes different from those of feature points 41, 42 and 43, they maintain their relative positions. The matching of the feature points of a model to modified feature points of a modified model provides at least two advantages. First, it saves time as the modified feature points are ascertained upon the modification of the model based on the MR data of a given patient. Second, it reduces subjectivity in assigning feature points on the MR image of a patient's anatomy, thus increasing the consistency and reproducibility of the ablation trajectory planning process even when the modification or adaption is administrated by different surgeons. In some implementations presented by FIGS. 5A, 5B and 5C, the feature points and modified feature points are triangular in shape. In some other implementations, the feature points and modified feature points can be of different geometric shapes. In some implementations, the features points can include one, two, three, or more individual polygons that form the 3D brain model. However, regardless of the shapes of the feature points/modified features points, each of the feature points/modified feature points is associated with one or more of the polygon in the 3D brain model or the modified 3D brain model.

Figure 6:
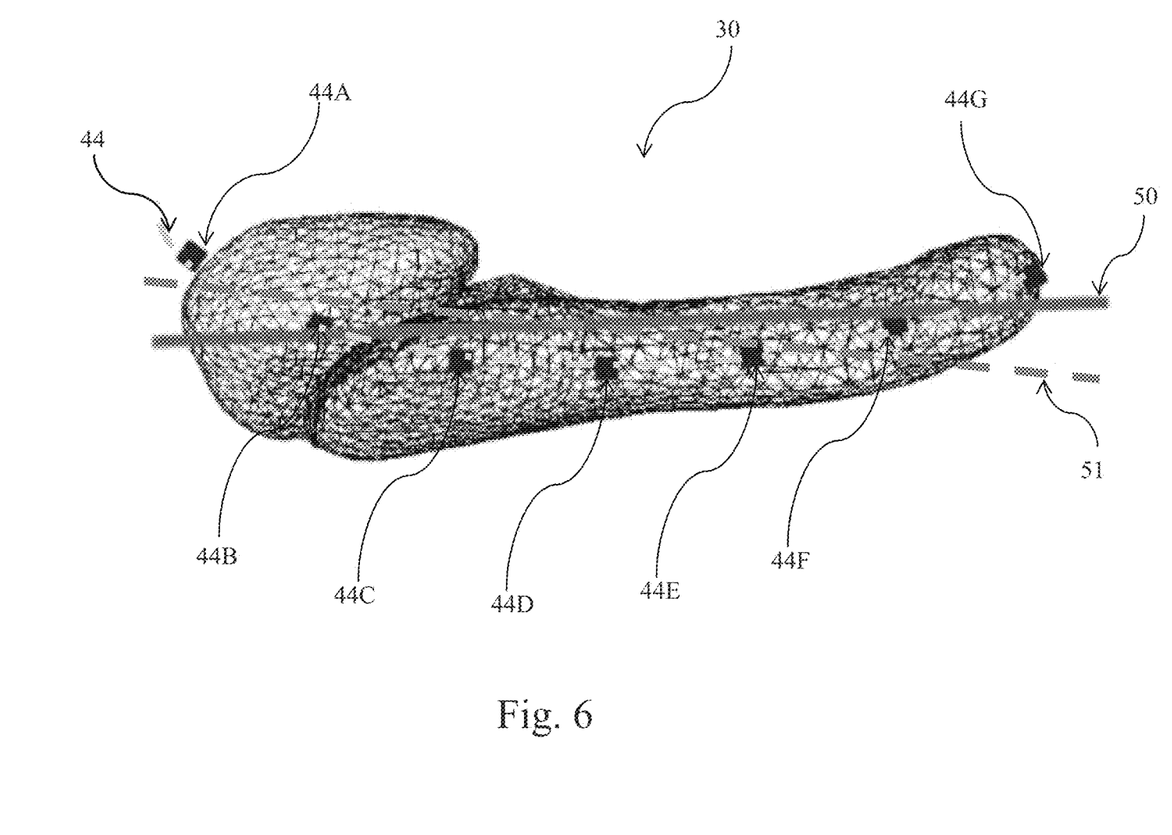
FIG. 6 is a schematic diagram of a modified model of a patient's AHC with modified feature points, according to aspects of the present disclosure.

At operation 208, a first planned trajectory for ablating a patient's anatomy based on the plurality of modified feature points is displayed on the display 150. Referring now to FIG. 6, which is a modified model of a patient's AHC 30. In some embodiments, once the modified model of the patient's AHC 30 with modified feature points 44A, 44B, 44C, 44D, 44E, 44F, and 44G are obtained and displayed on the display 150, the computing device 120 may identify a first planned trajectory 50 (or a preliminary planned trajectory 50 in this case) based on the type of the treatment device 140 and historical normative data of different ablation trajectories in relation to modified feature points and outcome of these ablation procedures. As shown in FIG. 6, in some implementations, the modified feature points 44A-44G form a curve and substantially fall on a geometric midline 44 of the patient's AHC. The geometric midline 44 is exemplary and any suitable path can be selected to designate the features points. In some embodiments represented by FIG. 6, the treatment device 140 enables straight trajectories, such as the first planned trajectory. In some other embodiments, the treatment device 140 may enable curved trajectories that better fit the curve formed by the modified feature points 44A-44G. In some other embodiments, a user, such as a surgeon, may use the user input device 130 to draw the first planned trajectory 50. In still some other embodiments, the computing device 120 may determine the trajectory 50 such that the trajectory 50 best approximates the modified feature points. In all these embodiments, the first planned trajectory 50 is identified, selected or drawn to address each of the modified feature points 44A-44G. In some implementations, the suggestion or selection of the first planned trajectory 50 may include other considerations. For example, the first planned trajectory 50 may be identified to traverse or avoid certain part of the brain to avoid undue damages to the brain.

For another example, the first planned trajectory 50 may be selected to minimize the path to the patient's brain, also to reduce damages to the brain. In some embodiments, the first planned trajectory 50 is displayed on the display 150 along with the modified model of the patient's AHC 30, as shown in FIG. 6. In other embodiments not shown in FIG. 6, the first planned trajectory 50 is displayed on the display 150 along with the modified 3D brain model of the patient's brain. In some embodiments, the first planned trajectory 50 is determined to be the final planned trajectory for ablating the patient's anatomy. Method 200 can skip operations 210, 212 and 214 and proceed directly to operation 216.

At operation 210, a first estimated ablation result for the first planned trajectory is displayed on the display 150. The ablation result here may sometimes be referred to as an ablation volume, which stands for the volume of brain tissues ablated or reduced by ablation. The estimated ablation result can be a numerical value, such as a percentage in some instances. In some embodiments, the computing device 120 can estimate the ablation result for the first planned trajectory 50 based on an estimated energy input of the treatment device 140. In some instance, the energy input can be estimated based on the power of the ablation catheter and the speed at which the ablation catheter travels through the first planned trajectory 50. Both of the power and speed of the ablation catheter can be controlled by the computing device 120 which is connected to and controls the catheter driver of the treatment device 140. In some embodiments, after operation 210, the first planned trajectory 50 is determined to be the final planned trajectory for ablating the patient's anatomy. Method 200 can skip operations 212 and 214 and proceed directly to operation 216.

At operation 212, in response to a first user input, a second planned trajectory 51 different from the first planned trajectory 50 is displayed on the display 150. To help the surgeon to identify an optimal trajectory, in some implementations, the computing device120 may propose a second planned trajectory 51 and display it on the display 150 in response to a first user input. In some other implementations, the user, such as the surgeon, may use the user input device 130 to draw the second planned trajectory 51 to be displayed on the display 150. The computing device 120 and the surgeon can determine which of the first and second planned trajectory better addresses the modified feature points and likely causes less damage to the patient's brain. In some embodiments, the second planned trajectory 51 is determined to be the final planned trajectory for ablating the patient's anatomy. Method 200 can skip operations 214 and proceed directly to operation 216.

At operation 214 of the method 200, a second estimated ablation result for the second planned trajectory is displayed on the display 150. In some embodiments, the computing device 120 can estimate the ablation result for the second planned trajectory 51 based on an estimated energy input of the treatment device 140. In some instance, the energy input can be estimated based on the power of the ablation catheter and the speed at which the ablation catheter travels through the second planned trajectory 51. Both of the power and speed of the ablation catheter can be controlled by the computing device which is connected to and controls the catheter driver of the treatment device 140. In some implementation, the computing device 120 can cause both the first estimated ablation result and the second estimated ablation result to be displayed on the display 150, by themselves or along with the modified model, as shown in FIG. 6. This way, the surgeon can better visualize the comparative efficacy of ablation along the first planned trajectory and along the second planned trajectory and therefore forms a more informed decision when choosing a final planned trajectory. After operation 214, the second planned trajectory 51 can be determined to be the final planned trajectory for ablating the patient's anatomy. Method 200 proceeds to operation 216.

Figure 7:
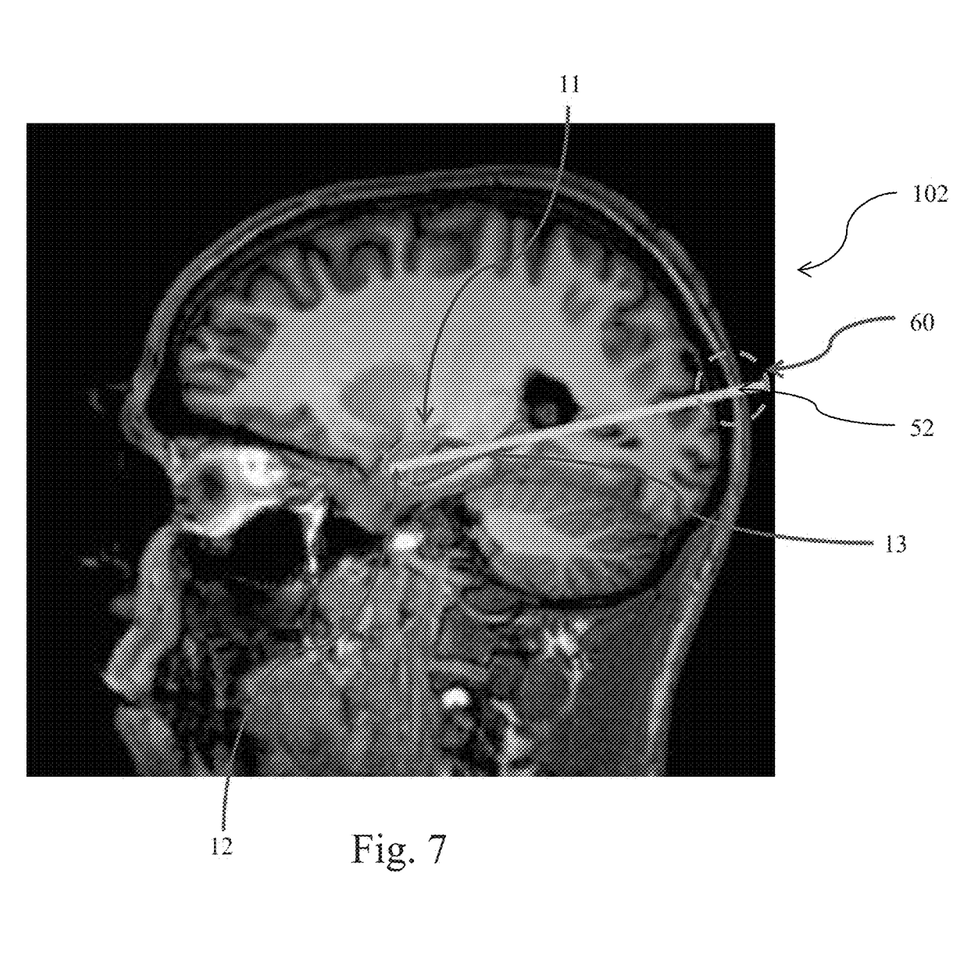
FIG. 7 is an MR image of a patient's brain showing the AHC and a planned trajectory, according to aspects of the present disclosure.

In some embodiments, besides displaying the planned trajectories and associated ablation results along with the modified models, the computing device 120 can overlay the first and second planned trajectories on a MR image of the patient's brain. Referring now to FIG. 7, shown therein is an MR image 102 of a patient's brain showing his/her AHC and a final planned trajectory 52. After the final planned trajectory 52 is determined, the computing device 120 can overlay the final planned trajectory 52 on the MR image 101 in FIG. 4 of the patient's brain to show the final planned trajectory 52 relative to the AHC 11, the amygdala 12 and the hippocampus 13. FIG. 7 also includes an entry point 60 where the final planned trajectory 52 intersects with the patient's skull. Once the entry point 60 is determined, the computing device 120 can estimate how far the alignment rod/ablation catheter travels in the patient's brain, when to energize the ablation catheter and when to de-energize the ablation catheter. Reference is now made to FIG. 6. In some embodiments, a user can cause the modified model of the patient's AHC 30 to three-dimensionally rotate to different orientation to help visualize the angles at which the first planned trajectory 50 or the second planned trajectory 51 approach the AHC 30 and the modified feature points 44A-44G.

At operation 216 of the method 200, an actual ablation trajectory is obtained by use of the MRI device 110 while actual ablation trajectory is being created according to the first planned trajectory 50 or second planned trajectory 51, whichever is determined to be the final planned trajectory 52. In some instances, the actual ablation trajectory is created by a craniotomy procedure followed by insertion of an alignment rod. After the actual ablation trajectory is created, the ablation catheter will track the actual ablation trajectory during the ablation procedure. In some implementations, MR data of the patient's brain is obtained in real time while the actual ablation trajectory is being created according to the final planned trajectory. In those implementations, MR data of the patient's brain obtained at intervals will show that the actual ablation trajectory is being created gradually from, for example, the entry point 60 shown in FIG. 7, to the amygdala 12 in FIG. 7.

At operation 218 of the method 200, both the actual ablation trajectory and the final planned trajectory are output by the computing device 120 to the display 150 for display. In some embodiments, the actual ablation trajectory is overlaid on the final planned trajectory to allow visual and/or quantitative comparison of the two. For example, at operation 218, the actual ablation trajectory (not shown) can be overlaid with the MR image 102. That way, as the actual ablation trajectory is being created, it is shown bit by bit along with the final planned trajectory 52. In some instances, the surgeon may be able to correct the trajectory based on the comparison presented at operation 218. In some other instances, the surgeon may perform a separate ablation procedure based on the comparison of the actual ablation trajectory and the final planned trajectory.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method for treatment trajectory guidance in a patient's brain, comprising:
accessing a three-dimensional (3D) brain model that includes a model of an anatomy, the model of the anatomy including a plurality of feature points;
modifying, by use of a computing device in communication with an magnetic resonance imaging (MRI) device, the 3D brain model based on magnetic resonance (MR) data of the patient's brain from the MRI device to obtain a plurality of modified feature points on a modified model of the patient's anatomy in the patient's brain, the modified feature points comprising one or more of points of therapeutic importance or points where neurons are concentrated in the patient's brain and associated with one or more polygons in the modified brain model;
generating a first planned trajectory for treating the patient's anatomy based on a treatment device and historical normative data of different trajectories in relation to the modified feature points and procedure outcomes, the first planned trajectory comprising an ablation trajectory addressing one or more of the modified feature points and curved based on a fit to the modified feature points;
displaying, on a display in communication with the computing device, the first planned trajectory; and
displaying, on the display, a first estimated treatment result for the first planned trajectory.

2. The method of claim 1, wherein the first planned trajectory comprises a first entry point into the patient's brain.

3. The method of claim 1, further comprising:
in response to a first user input, displaying on the display a second planned trajectory different from the first planned trajectory; and
displaying on the display a second estimated treatment result for the second planned trajectory.

4. The method of claim 1, further comprising:
obtaining, by use of the MRI device, an actual treatment trajectory during a treatment of the patient's anatomy; and
displaying, on the display, the actual treatment trajectory along with the first planned trajectory.

5. The method of claim 1, wherein the MR data comprise T1 weighted magnetic resonance (T1W MR) data of the patient's brain.

6. The method of claim 1, wherein the 3D brain model is a shape-constrained deformable brain model.

7. The method of claim 1, wherein the plurality of feature points extend along a geometric midline of the model of the anatomy.

8. The method of claim 1, wherein the patient's anatomy comprises an amygdalohippocampal complex, an amygdala, a hippocampus, a lesion, or a tumor in the patient's brain.

9. A treatment trajectory guidance system, comprising:
a computing device in communication with a magnetic resonance imaging (MRI) device, the computing device operable to:
access a three-dimensional (3D) brain model that includes a model of an anatomy, the model of the anatomy including a plurality of feature points;
receive magnetic resonance (MR) data of a patient's brain from the MRI device;
modify the 3D brain model based on the MR data of the patient's brain to obtain a plurality of modified feature points on a modified model of the patient's anatomy, the modified feature points comprising one or more of points of therapeutic importance or points where neurons are concentrated in the patient's brain and associated with one or more polygons in the modified brain model;
generate a first planned trajectory for treating the patient's anatomy based on a treatment device and historical normative data of different trajectories in relation to the modified feature points and procedure outcomes, the first planned trajectory comprising an ablation trajectory addressing one or more of modified feature points and curved based on a fit to the modified feature points;
output, to a display in communication with the computing device, the first planned trajectory; and
output to the display a first estimated treatment result for the first planned trajectory.

10. The treatment trajectory guidance system of claim 9, wherein the first planned trajectory comprises a first entry point into the patient's brain.

11. The treatment trajectory guidance system of claim 9, wherein the computing device is further operable to:
in response to a first user input, display on the display a second planned trajectory different from the first planned trajectory; and
display on the display a second estimated treatment result for the second planned trajectory.

12. The treatment trajectory guidance system of claim 9, wherein the computing device is further operable to:
obtain, by use of the MRI device, an actual treatment trajectory during a treatment of the patient's anatomy; and
output, to the display, the actual treatment trajectory along with the first planned trajectory.

13. The treatment trajectory guidance system of claim 9, further comprising the display and the MRI device.

14. The treatment trajectory guidance system of claim 9, wherein the MR data comprise T1 weighted magnetic resonance (T1W MR) data of the patient's brain.

15. The treatment trajectory guidance system of claim 9, wherein the brain model is a shape-constrained deformable brain model.

16. The treatment trajectory guidance system of claim 9, wherein the plurality of feature points extend along a geometric midline of the model of the anatomy.

17. The treatment trajectory guidance system of claim 9, wherein the patient's anatomy comprises an amygdalohippocampal complex, an amygdala, a hippocampus, a lesion, or a tumor in the patient's brain.

18. A non-transitory computer readable medium storing instructions that, when executed by one or more processors, cause the one or more processors to:
access a three-dimensional (3D) brain model that includes a model of an anatomy, the model of the anatomy including a plurality of feature points;
modify the 3D brain model based on magnetic resonance (MR) data of the patient's brain from a magnetic resonance imaging (MRI) device to obtain a plurality of modified feature points on a modified model of the patient's anatomy in the patient's brain, the modified feature points comprising one or more of points of therapeutic importance or points where neurons are concentrated in the patient's brain and associated with one or more polygons in the modified brain model;

generate a first planned trajectory for treating the patient's anatomy based on a treatment device and historical normative data of different trajectories in relation to the modified feature points and procedure outcomes, the first planned trajectory comprising an ablation trajectory addressing one or more of the modified feature points and curved based on a fit to the modified feature points; and display the first planned trajectory and a first estimated treatment result for the first planned trajectory.

19. The non-transitory computer readable medium of claim 18, further comprising instructions to:

in response to a first user input, display a second planned trajectory different from the first planned trajectory; and display a second estimated treatment result for the second planned trajectory.

20. The non-transitory computer readable medium of claim 18, wherein the 3D brain model is a shape-constrained deformable brain model.

* * * * *